US007785788B2

(12) United States Patent
Xie

(10) Patent No.: US 7,785,788 B2
(45) Date of Patent: Aug. 31, 2010

(54) METHOD FOR THE DETECTION OF RISK FACTORS ASSOCIATED WITH MYOCARDIAL INFARCTION

(75) Inventor: Ya-Gang Xie, Saint John's (CA)

(73) Assignee: New Lab Clinical Research Inc., St. John's (CA)

( * ) Notice: Subject to any disclaimer, the term of this patent is extended or adjusted under 35 U.S.C. 154(b) by 376 days.

(21) Appl. No.: 11/428,829

(22) Filed: Jul. 5, 2006

(65) Prior Publication Data

US 2006/0252084 A1 Nov. 9, 2006

Related U.S. Application Data

(63) Continuation of application No. 10/735,600, filed on Dec. 12, 2003, now abandoned.

(30) Foreign Application Priority Data

Dec. 13, 2002 (CA) .................................. 2414301

(51) Int. Cl.
*C12Q 1/68* (2006.01)
*C12P 19/34* (2006.01)
(52) U.S. Cl. .......................................... 435/6; 435/91.1
(58) Field of Classification Search ........................ None
See application file for complete search history.

(56) References Cited

U.S. PATENT DOCUMENTS

| 5,620,688 A | 4/1997 | Reed et al. |
| 5,766,869 A | 6/1998 | Arkel et al. |
| 5,834,223 A | 11/1998 | Griffin et al. |
| 5,874,256 A | 2/1999 | Bertina et al. |
| 5,910,576 A | 6/1999 | Bertina et al. |
| 6,040,147 A | 3/2000 | Ridker et al. |
| 6,043,035 A | 3/2000 | Bertina et al. |
| 6,083,757 A | 7/2000 | Griffin et al. |
| 6,147,078 A | 11/2000 | Sanderson et al. |
| 6,183,980 B1 | 2/2001 | Siegemund et al. |
| 6,221,898 B1 | 4/2001 | Antonsson |
| 6,239,132 B1 | 5/2001 | Coburn et al. |
| 6,350,745 B1 | 2/2002 | Coburn et al. |
| 6,376,499 B1 | 4/2002 | Sanderson et al. |

FOREIGN PATENT DOCUMENTS

| CA | 2347247 A3 | 4/2000 |
| EP | 0200362 B1 | 10/1986 |
| EP | 0201184 B2 | 12/1986 |

OTHER PUBLICATIONS

Ionnidis (Plost Med, 2005, 2(8):e124, pp. 696-701).*
Kroese et al. (Genetics in Medicine, vol. 6 (2004), p. 475-480).*
Mummidi et al., J Biol. Chem, 2000, vol. 275, pp. 18946-18961.*
Restriction Requirement dated Apr. 5, 2006 issued in U.S. App. No. 10/735,600.
Franco. Rendrik F. et al., "Factor XIII Val34Leu and the risk of myocardial infarction", Haematologica, Jan. 2000, vol. 85, No. 1, pp. 67-71.
Kangsadalampai, S. et al., "The Val34Leu polymorphism in the A subunit of coagulation factor XIII contributes to the large normal range in activity and demonstrates that the activation peptide plays a role in catalytic activity", Blood, 1998, col. 92, pp. 2766-2770.
Amowitz, et al.;(1999) Factor V Leiden is Not a Risk Factor for Myocardial Infarction Among Young Women; Correspondence, pp. 1432-1433.
Ardissino,D.,et al.,(1999)Prothrombotic Genetic Risk Factors in Young Survivors of Myocardial Infarction;Blood;vol. 94,No. 1,pp. 46-51.
Ariens, R. et al.,(2000)The factor XIII V34L polymorphism accelerates thrombin activation of factor XIII and affects cross-linked fibrin structure;Blood,vol. 96,No. 3,pp. 988-995.
Arruda, V et al., (1998) Prevalence of the prothrombin gene variant 20210 G- A among patients with myocardial infarction; Cardiovascular Research 37,pp. 42-45.
Bitondo,R.D. et al.,(2001) The-1185 A/G and 1051 G/A dimorphisms in the von Willebrand factor gene promoter and risk of myocardial infarction;British Journal of Haematology,vol. 115,pp. 701-706.
Bird,et al.,(1988)Single-Chain Antigen-Binding Proteins; Science,vol. 242,pp. 423-426.
Brown,K.,(1997)Risk of veneous thromboembolism associated with a G to A transition at posit;Br.J.Haematol,98 (4):907-909.
Butt,C.,et al.,(2003) Combined carrier status of prothombin 20210A and factor XIII-A Leu34 alleles as strong risk factor for myocardial infarction:evidence of a gene-gene interaction;Blood,101(8):3037-3041.Epub Dec. 12, 2002.
Corral,J.et al.,(2001)Polymorphisms of clotting factors modify the risk for primary intracranial hemorrahge; Blood,vol. 97,No. 10,pp. 2979-2982.
Doggen,J.M. et al.,(1998) Increased Risk of Myocardial Infarction Associated with Factor V Leiden or Proththrombin 20210A;American Heart Association, Inc.pp. 1037-1041.
Eikkelboom,J.W. et al.,(1998)No association between the 20210 G/A prothrombin gene mutation and premature coronary artery disease;Thromb-Haemost.,80(6):878-80.
Faham M and Cox D.R.,(1995)A novel in vivo method to detect DNA sequence variation;Genome Res.(5):474-82.
Franco,R.F.,et al.(1999) The 20210G → A mutation in the 3'-unstranslated region of the prothrombin gene and the risk for arterial thrombotic disease; British Journal of Haematology, vol. 104, pp. 50-54.
Franco, R.F., et al. (2000) Factor XIII val34eu and the risk of myocardial infarction; Haematologica, 85(1): 67-71.
Franco, R.F. and Reitmsma, P.H. (2001) Genetic risk factors of venous thrombosis; Human Gentics,109(4):369-84.
Frizner,S.J.et al.,(1987)Nucleotide sequence of the gene for human prothrombin;Biochemistry.,(19);6165-6177.

(Continued)

Primary Examiner—Sarae Bausch
(74) Attorney, Agent, or Firm—Birch, Stewart, Kolasch & Birch, LLP

(57) ABSTRACT

A method for determining whether an individual is at an increased risk for myocardial infarction, comprising screening for the presence of Factor II and Factor XIII alleles associated with myocardial infarction. Also provided are kits and primers that specifically hybridize adjacent to the allele-specific regions of the Factor II and Factor XIII genes.

9 Claims, 6 Drawing Sheets

OTHER PUBLICATIONS

Gauderman J.W., (2002) Sample Size Requirements for Association Studies of Gene Interaction; American Journal of Epidemiology, vol. 155, No. 5, pp. 478-484.

Huston et a., (1988) Protein engineering of antibody binding sites: recovery of specific activity in an anti-digoxin single chain Fv analogue produced in *Escherichia coli*; ProcNatl Aca Sci, 85(16): 5879-83.

Kohler, H.P., et al. (1998) Association of a common polymorphism in the factor XIII gene with myocardial infarction; Throm-Haemost., 79(1): 8-13.

Linfert D.R., et al. (1998) Rapid multiplex analysis for the factor V Leiden and prothrombin G20210A mutations associated with hereditary thrombophilia.Conn.Med., 62(9): 519-525.

Lung, C.C. and Chan, K.L. (1996) Simplifying 5' RACE in the hunt far full-length cDNAs. Trends in Genetics, 12,389-391.

Mansourati, J., (2000) Prevalence of factor V Leiden in patients with myocardial infarction and normal coronary angiography. Thromb-Haemost., 83(6): 822-5.

Miller S.A., et al., (1988) A simple salting out procedure for extracting DNA from human nucleated cells. Nulceic Acids Research; 16(3): 1215.

Poort, (1996) A common genetic variation in the 3'-unstranslated region of the prothrombin gene is associated with elevated plasma prothrombin levels and an increase in venous thrombosis; Blood 88 (10): 3698-3703.

Ridker, P>M>, et al., G20210A Mutation in Prothrombin Gene and Risk of Myocardial Infarction, stroke and Venous Thrombosis in a Large Cohort of US Men; Circulation, (8): 999-1004, 1999.

Rosendaal, (1997) A Common Prothrombin Variant (2020 G to A) Increases the Risk of Myocardial Infarction in young Women; Blood; 90(5) 1747-1750.

Russo, C., et al., (2001) G 20210 A Prothrombin Gene Polymorphism and Prothrombin Activity in Subjects with or Without Angiographically Documented Coronary Artery Disease; Circulation, 103 (20): 2436-40.

Saiki et al., (1988) Science 239, 487.

Sanger (1977) Proc. Natl. Acad. Sci. USA, 74 5463-7.

Tetrahedron Letters 22, (1981) 1859-1862.

Thrombosis and Homeostasis 78, (1977) 1157-1163.

Trumbo, T.A. and Maurer M.C., (2000) Examination Thrombin Hydrolysis of Factor XIII Activation Peptide Segment Leads to a Proposal for Explaining the Cardio protective Effects Observed with the Factor XIII V34L Mutation; The Journal of Biological Chemistry, vol. 275, No. 27, pp. 20627-20631.

Trumbo, T.A. and Maurer M.C., (2002) Thrombin Hydrolysis of V29F and V34L Mutants of Factor XIII (28-41) reveals Roles of the P9 and P4 Positions in Factor XIII Activation; Biochemistry, vol. 41, 2859-2868.

Van de Water, N. S., et al., (2000) Prevalence of Factor V Leiden and Prothrombin Variant G20210A in Patients Age <50 Years with No Significant Stenoses at Angiography Three to Four Weeks After Myocardial Infarction; Journal of the American College of Cardiology, vol. 36, No. 3, pp. 717-722.

Wagner et al. (1995) Mutation detection using immobilized mismatch binding protein (MutS); Nucl acids res, 23(19): 3944-3948.

Ward et al., (1989) Nature 341:544-546.

Warner, D.et al., (2001) Coagulation factor XIII and cardiovascular disease in UK Asian patients undergoing coronary angiography; Thromb-Haemost, 8593): 408-11.

Wartiovaara, U. et al., (1999) Association of FXIII Val34Leu with decreased risk of myocardial infarction in Finnish Wartiovaara; U Atherosclerosis, 142(2): 295-300.

Weger, M et al., (2003) Role of factor V Leiden and prothrombin 20210A in patients with retinal artery occlusion; 17 (6): 731-4.

\* cited by examiner

METHOD FOR THE DETECTION OF RISK FACTORS ASSOCIATED WITH MYOCARDIAL INFARCTION

CROSS-REFERENCE TO RELATED APPLICATION

This application is a Continuation of co-pending application Ser. No. 10/735,600, filed on Dec. 12, 2003, the entire contents of which are hereby incorporated by reference and for which priority is claimed under 35 U.S.C. §120.

FIELD OF THE INVENTION

The present invention relates to the field of myocardial infarction, more particularly, the invention is directed at a method for determining the risk for myocardial infarction in an individual.

BACKGROUND OF THE INVENTION

Myocardial infarction (MI) is now among the most frequent causes of illness and death, especially in the industrial countries. If myocardial infarction is survived, the vitality of the patient is limited in most cases, by secondary symptoms such as paralysis or organ damage. There are also labor-intensive and cost-intensive follow-up treatments, such as convalescence, physiotherapy and medication to improve the health situation and prevent further complications.

Great advances have been made in recent years, especially in research into the causes of myocardial infarction, and these include cardiac tissue necrosis caused by an inadequate blood supply due to the occlusion of arterial blood vessels either by cholesterol plaque build-up, or by clot blockage (thrombosis). Risk factors for thrombosis-induced myocardial infarction are thought to include both hereditary and acquired conditions.

Generally, a tendency towards myocardial infarction could arise from hyperactive coagulation pathways, hypoactive anticoagulant mechanisms, or hypoactive fibrinolysis. Mutations in genes that encode proteins in these pathways are thought to play an important role in the predisposition to myocardial infarction.

The serine protease thrombin formed by cleavage of human prothrombin (also known as Factor II (FII)) exerts a central action to the processes of thrombosis and haemostasis. The thrombin molecule plays a role in the final stage of blood coagulation: the formation of an insoluble fibrin clot.

The hitherto known congenital disorders of prothrombin are rare and involve either reduced synthesis of the FII molecule (referred to as hypoprothrombinemia or type I prothrombin deficiency) or the normal synthesis of a dysfunctional molecule (referred to as dysprothrombinemia or type II prothrombin deficiency). Patients with dysprothrombinemia have only 2% to 50% of the clotting activity of normal prothrombin; in these patients the severity of the bleedings correlates fairly well with the amount of prothrombin activity in plasma. A number of dysprothrombinemias have been further characterized by amino acid sequence analysis of the isolated prothrombin molecule or by nucleotide sequence analysis of their prothrombin genes.

It is known that the gene variant Factor V Leiden (FVL-R506Q, or FVL) and prothrombin G20210A (FIIG20210A) are two of the most commonly recognized genetic prothrombic risk factors for venous thrombosis. Based on the increased thrombotic tendency in venous thrombosis studies, these two gene variants have also been examined for possible association with arterial thrombosis in myocardial infarction. The prothrombin variant G20210A, comprising a G to A transition mutation at nucleotide 20210 is a very good example. This point mutation is associated with increased prothrombin levels that lead to an increased risk of thrombosis (Poortn, Blood 1996; 88 (10): 3698-703). Publications indicate an increased risk of cardiac infarctions (Rosendahl, Blood 1997; 90(5) 1747-50) and venous thromboses (Brown, Br. J. Haematol; 98(4): 907-9). However, it has also been possible to demonstrate that discrimination between mutation carrier and the wild type is not possible on the basis of the prothrombin level, since the two groups cannot be separated (Poortn, Blood 1996; 88(10): 3698-703).

Several studies have shown higher prevalence of FIIG20210A in patients with myocardial infarction compared to normal controls. However, most of the results from these studies failed to achieve statistical significance, possible because of the extremely low frequency of FIIG20210A in the studied population and the use of relatively small sample sizes. Nevertheless, a few studies have presented conflicting results.

Although FVL strongly correlates with deep venous thrombosis, the majority of the previous studies have failed to show a correlation of FVL to myocardial infarction. Recently, a few studies have suggested that FVL may associate with early onset myocardial infarction and myocardial infarction with normal coronary angiography.

In contrast, a common gene variant, Factor XIIIV34L (FXIIIV34L) has recently been suggested to confer a protective role against myocardial infarction based on lower prevalence of FXIIIV34L in myocardial infarction patients compared with controls. However, conflicting results were also reported. Furthermore, results from function studies on the FXIIIV34L allele do not support the hypothesis of a protective role against myocardial infarction. Therefore, the role of these gene variants in the pathogenesis of myocardial infarction remains unknown.

Furthermore, no cause of myocardial infarction is detectable in a high proportion of all cases. If such defects exist, the hemostatic equilibrium is disturbed and the ratio between pro- and anticoagulatory factors is shifted in favor of one side. To this are added defects in the fibrinolysis system that reduce the breakdown of clots formed.

Being a multifactorial disorder, myocardial infarction may be a combined effect of a number of genes, with each playing only a small role. The predisposition imparted by individual genes may act independently or interact with other genes to result in an additive effect and/or a synergistic co-effect. Common challenges facing case control studies on possible gene-gene interactions include relatively small sample sizes, a low frequency of gene variants, and ethnic heterogeneity of the investigated population.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

In one aspect, the present invention provides methods for determining a risk factor for myocardial infarction. These methods comprise assaying a suitable biological sample and determining the presence or absence of variant genetic elements, their gene products, or altered physiochemical activities of these gene products correlated with elevated risk of myocardial infarction.

In one embodiment, the invention provides a method in which said genetic elements are a mutation in the gene encoding FII, more particularly a G to A transition mutation at nucleotide position 20210 (FIIG20210A), and a mutation in the FXIII gene, more particularly a valine to leucine substitution mutation at amino acid position 34 (FXIIIV34L). It is to be understood that other genetic elements, coding for the components of the fibrinolysis system, the clotting system, and the complement system, can be similarly analyzed to determine a correlation with an elevated risk for myocardial infarction. In another aspect the present invention provides a kit for use in said method.

The present invention also provides a first nucleotide sequence comprising at least part of the nucleotide sequence of the human FIIG20210A allele, a second nucleotide sequence comprising at least part of the nucleotide sequence of the human FXIIIV34L allele, and a third nucleotide sequence comprising at least part of the nucleotide sequence of the human FVL allele, as well as the use of such sequences for the detection of such mutations. The present invention also provides primers for the allele specific detection of these mutations of the FII gene at nucleotide 20210, the FXIII gene at amino acid 34, and the FV gene at amino acid 506.

In accordance with one aspect of the present invention, there is provided a method of determining a risk for myocardial infarction, or a propensity therefor in an individual comprising:

(a) obtaining a biological sample from an individual; and
(b) analysing said biological sample for the presence of a variant of a gene encoding Factor II, Factor V, Factor XIII or a combination thereof.

In accordance with another aspect of the present invention, there is provided a method for the detection of defects in a multi-stage, multi-factorial biochemical reaction system, wherein the defects are associated with an increased risk of myocardial infarction in an individual, comprising the steps of:

a) screening for suitable patients at risk of myocardial infarction, wherein said screening is conducted on the basis of a family history or individual case history;
b) obtaining a suitable biological sample from the individual;
c) determining the presence of variant genetic elements, the gene products of said variant genetic elements, or altered physiochemical activities of said gene products known to be correlated with myocardial infarction; and
d) determining the risk to the individual of myocardial infarction.

In accordance with another aspect of the present invention, there is provided a method for determining whether an individual is at an increased risk for myocardial infarction, comprising detecting the presence or absence of mutations in genetic elements, aberrant gene products of genetic elements or altered physiochemical activity of the gene products of genetic elements, wherein said genetic elements are correlated with an elevated risk for myocardial infarction.

In accordance with another aspect of the present invention, there is provided a method for determining whether an individual is at an increased risk for myocardial infarction, comprising determining Factor II and Factor XIII genetic element sequences of an individual, whereby the presence of a G20210A mutation in a Factor II gene sequence, and the presence of a V34L mutation in a Factor XIII gene sequence is indicative of an increased risk for myocardial infarction in said individual.

In accordance with another aspect of the present invention, there is provided a method for determining whether an individual is at an increased risk for myocardial infarction, comprising determining gene products of Factor II and Factor XIII genetic elements of an individual, whereby the presence of FIIG20210A and FXIIIV34L gene products is indicative of an increased risk for myocardial infarction in said individual.

In accordance with another aspect of the present invention, there is provided a method for determining whether an individual is at an increased risk for myocardial infarction, comprising determining physiochemical activity of gene products of the Factor II and Factor XIII genetic elements of an individual, whereby the presence of FIIG20210A and FXIIIV34L gene products' physiochemical activity is indicative of an increased risk for myocardial infarction in said individual.

In accordance with another aspect of the present invention, there is provided a kit for determining whether an individual is at an increased risk for myocardial infarction, comprising oligonucleotides specific to the variant region of the alleles of interest or to sequence flanking the variant region and optionally instructions for use.

DETAILED DESCRIPTION OF THE INVENTION

Figure 1A:
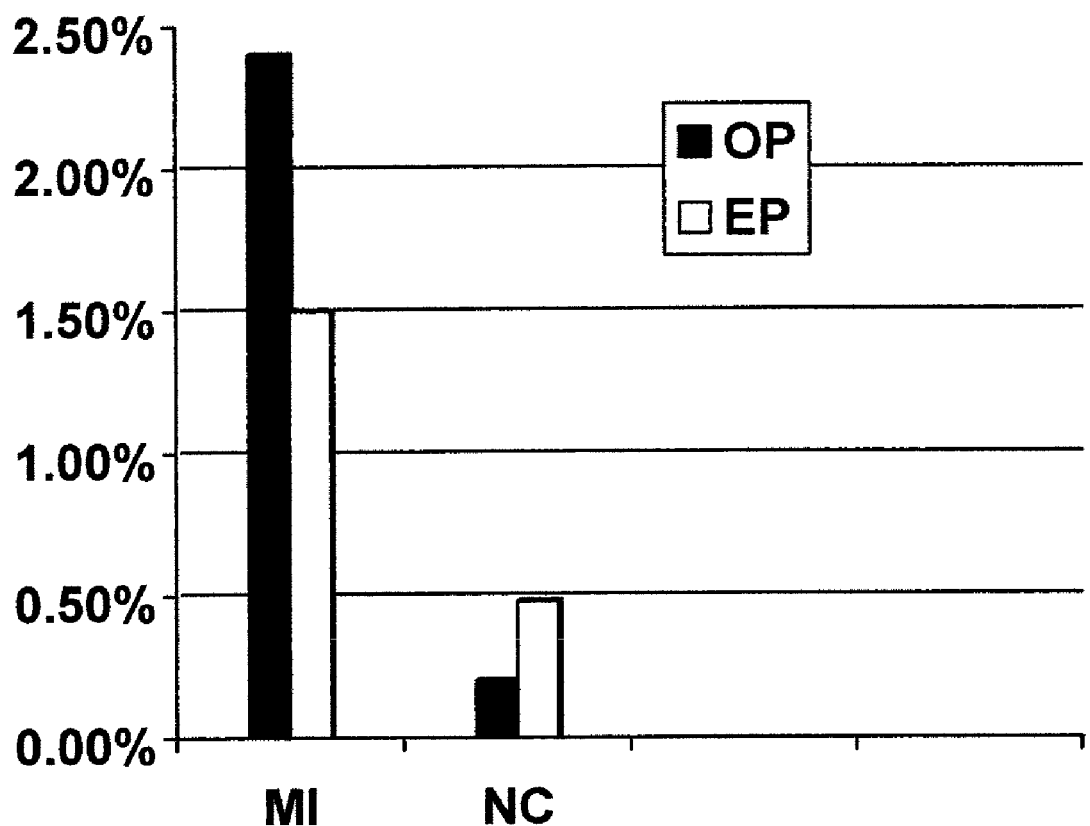
FIG. 1 shows a comparison between expected and observed prevalence of combined carriers of mutations in myocardial infarction as described in Example 1 (MI=500 individuals, control=500 individuals)

The present invention provides for methods of identifying risk factors associated with myocardial infarction. The invention further provides for the application of these identified risk factors in methods of identifying individuals at risk for myocardial infarction or individuals having a propensity for myocardial infarction. Thus, the present invention provides diagnostic and prognostic tools valuable in a medical context. In the context of the present invention, a "risk factor" refers to a variant genetic element, typically a mutation, the presence of which in an individual's genome provides an indication of increased risk for myocardial infarction. The presence of such variant genetic elements can be determined at the genetic (nucleic acid) level or at the protein (polypeptide) level. In accordance with the invention, the risk factors comprise a variant of one or more genes encoding proteins that are part of a multi-stage, multi-factorial biochemical reaction system, such as the fibrinolysis system, the clotting system, or the complement system.

Definitions

Unless defined otherwise, all technical and scientific terms used herein have the same meaning as commonly understood by one of ordinary skill in the art to which this invention belongs.

The term "genetic element", as used herein, refers to a nucleotide sequence present in the genome of the organism under investigation. Examples of genetic elements correlated with elevated myocardial infarction risk comprise, but are not restricted to, genes coding for components of the fibrinolysis system, the clotting system, or the complement system, such as, for example, the genes coding for FII, FV, and FXIII.

"Mutations" in these genes contemplated by the invention include, but are not limited to, deletions, insertions, chromosomal dislocations, translocations, inversions, and other genetic mechanisms.

Method for the Identification of Risk Factors Associated with Myocardial Infarction Genetic elements and variants thereof associated with an elevated risk of myocardial infarction may be identified by methods known in the art. One strategy to identify said genetic elements and variants thereof encompasses the steps of sequencing a candidate gene in a panel of probands from families with documented myocardial infarction, followed by estimating the risk factor for myocardial infarction associated with any observed sequence variation in a population based patient-control study.

A non-limiting example of such a strategy is provided as Examples 1 and 2, which set forth the inventors' case control study, simultaneously analyzing for the presence of the FVL, FIIG20210A and FXIIIV34L variants in myocardial infarction patients and normal individuals of a genetically isolated population of the island portion of Newfoundland and Labrador.

Thus, the present invention relates to a method for the identification of one or a plurality of variant genetic elements that encode proteins that are part of a multi-stage, multi-factorial biochemical reaction system such as the fibrinolysis system, the clotting system, or the complement system, wherein the defects are associated with an increased risk of myocardial infarction in an individual. As used herein, "a plurality" refers to two or more. In one embodiment, the invention provides methods for the detection of one or a plurality of variant genetic elements that encode proteins that are part of the fibrinolysis system, the clotting system, and/or the complement system. In another embodiment, the invention provides methods for the detection of a plurality of variant genetic elements that encode proteins that are part of the fibrinolysis system, the clotting system, and/or the complement system, wherein the plurality of variant genetic elements indicate that an individual is at greater risk than any one of the variant genetic elements alone.

The methods of identifying the variant genetic elements provided by the present invention comprise the steps of identifying a suitable sample population of individuals to screen, obtaining a biological sample from each individual in the sample population, determining gene sequences, gene products of genes, or activities of gene products to identify variants thereof, and comparing the occurrence of the variants with the occurrence in a suitable reference population. A suitable sample population, for example, would be made up of individuals who have suffered myocardial infarction and a reference population would be made up of individuals who had no history (either individual or familial) of myocardial infarction. The sample population may be geographically restricted, restricted by age, gender or ethnicity if desired. Typically when a sample population is thus restricted the reference population is similarly restricted (i.e. matched) by geographical region, age, gender or ethnicity.

Once the sample and reference populations are selected, a suitable biological sample must be obtained in order to carry out the analysis for variant genetic elements. Biological samples obtained from a subject may comprise genomic DNA, RNA, or protein. For the purposes of physiochemical analysis, a suitable biological sample may be a blood or blood plasma sample containing the protein of interest. For the purposes of nucleic acid analysis, a suitable biological sample may be a blood or blood plasma sample, urine, saliva, tissue biopsy, surgical specimen, fine needle aspirates, amniocentesis samples, or any other material comprising the patient's genomic DNA. Methods for obtaining suitable biological samples are known in the art.

Detection of mutations may be performed, inter alia, by methods known in the art, such as direct sequence analysis of amplified nucleic acid containing the aberration, by allele specific amplification which differentially amplifies DNA containing and DNA lacking the aberration, or by restriction fragment analysis. It may also be performed by hybridization with a probe that is able to differentially hybridize under stringent conditions to the stretch of amplified nucleic acid material which may contain the aberration.

Various techniques for amplifying nucleic acid are known in the art. One example of a technique for the amplification of a DNA target segment is the polymerase chain reaction (PCR). With the PCR technique the copy number of a particular target segment is increased exponentially with a number of cycles. A pair of primers is used and in each cycle a DNA primer is annealed to the 3' side of each of the two strands of the doubled stranded DNA-target sequence. The primers are extended with a DNA polymerase in the presence of the various mononucleotides to generate double stranded DNA. The strands of the double stranded DNA are separated from each other by thermal denaturation and each strand then serves as a template for primer annealing and subsequent elongation in a following cycle. The PCR method has been described in Saiki et al., Science 239, 487, 1988 and in European Patents no. EP 200 362 and EP 201 184. Other amplification techniques include mismatch PCR, the Ligase Chain Reaction (LCR), Repair Chain Reaction (RCR), TMA, rolling circle amplification, nucleic acid sequence based amplification (NASBA), and strand displacement amplification (SDA).

The term "oligonucleotide" as used herein refers to a linear polynucleotide molecule of up to about 200 nucleotide bases in length, for example a polynucleotide (such as DNA or RNA) which is at least about 10 nucleotides, for example at least 15, 50, 100 or 200 nucleotides long. These oligonucleotides may function as primers and probes.

The term "primer" as used herein refers to an oligonucleotide either naturally occurring (e.g. as a restriction fragment) or produced synthetically, which may act as a point of initiation of synthesis of a primer extension product and which is able to hybridize to a nucleic acid strand (template or target sequence) when placed under suitable conditions (e.g. buffer, salt temperature and pH) in the presence of nucleotides and an agent for nucleic acid polymerization, such as DNA dependent or RNA dependent polymerase. A primer must be sufficiently long to prime the synthesis of extension products in the presence of an agent for polymerization. A typical primer contains at least about 10 nucleotides of a sequence substantially complementary or homologous to the target sequence, but somewhat longer primers are preferred. Usually primers contain about 15-26 nucleotides, but longer primers may also be employed. Normally a set of primers will consist of at least two primers, one 'upstream' and one 'downstream' primer which together define the sequence that will be amplified using said primers. The primers used for amplification of the various regions of the target genes may be synthesized by the methoxyphosphoramite method (Tetrahedron Letters 22, 1859-1865, 1981) or other suitable method known in the art. The sequences of the primers are chosen such that they flank the aberrant regions of the target gene. Suitable primers for amplification of the various transcribed and untranscribed regions of the alleles of interest are those determined to be most efficacious for the task.

Stringent (hybridization) conditions are conditions under which a test nucleic acid molecule will hybridize to a target reference nucleotide sequence, to a detectably greater degree than other sequences (e.g., at least two-fold over background). Stringent conditions are sequence-dependent and will differ in experimental contexts. For example, longer sequences hybridize specifically at higher temperatures. Generally, stringent conditions are selected to be about $5°$ C. to about $20°$ C. lower, and preferably, $5°$ C. lower, than the thermal melting point (Tm) for the specific target sequence at a defined ionic strength and pH. The Tm is the temperature (under defined ionic strength and pH) at which 50% of a complementary target sequence hybridizes to a perfectly matched probe. Typically, stringent conditions will be those in which the salt concentration is less than about 1.0 M Na ion concentration (or other salts), typically about 0.01 to 1.0 M Na ion concentration (or other salts), at pH 7.0 to 8.3, and the temperature is at least about $30°$ C. for short probes (e.g., 10 to 50 nucleotides) and at least about $60°$ C. for long probes (e.g., greater than 50 nucleotides). Stringent conditions may also be achieved with the addition of destabilizing agents such as formamide. Exemplary low stringency conditions include hybridization with a buffer solution of 30% formamide, 1 M NaCl, 1% SDS at $37°$ C., and a wash in 2 times SSC at $50°$ C. Exemplary high stringency conditions include hybridization in 50% formamide, 1 M NaCl, 1% SDS at $37°$ C., and a wash in 0.1 times SSC at $60°$ C.

The term "probe" refers to an oligonucleotide, typically labeled, that forms a duplex structure with a sequence of a target nucleic acid due to complementary base pairing. The probe will comprise a hybridizing region, preferably consisting of 10 to 50 nucleotides, more preferably 20 to 30 nucleotides, corresponding to a region of the target sequence. The hybridizing region of a probe is preferably identical or fully complementary to the sequence of the target region. The hybridizing region may also contain a certain number of mismatches, those skilled in the art of nucleic acid technology can determine duplex stability considering a number of variables including the length and base-pair composition of the probe, ionic strength of the buffer, reaction temperature and incidence of mismatched base pairs, see, e.g. Sambrook et al., Molecular cloning: A laboratory manual, second edition (1989) Cold Spring Harbor Laboratory Press.

The term "label" as used herein refers to any atom or molecule which can be attached to a nucleic acid and which can be used either to provide a detectable signal or to interact with a second molecule to modify the detectable signal provided by said second molecule. Examples of suitable labels include, but are not limited to, radioisotopes, fluorescent compounds, enzymes or chemiluminescent compounds.

Hybridization of the probe with the target sequence may be detected by techniques known in the art of nucleic acid technology such as Northern or Southern blotting, see e.g. Sambrook et al., supra. Detection systems that maybe used in conjunction with such methods include, for example, enhanced chemiluminescence (ECL) based analysis or enzyme linked gel assay (ELGA) based analysis.

Sequence analysis includes direct analysis of the DNA sequence flanking and constituting the exons and untranslated regions of the gene. This method involves any protocol that is currently available to any person skilled in the art for directly determining DNA- or RNA sequences, such as the dideoxynucleotide method described by Sanger (Proc. Natl. Acad. Sci. USA, 74 5463-7, 1977).

It is also possible to analyze the amplified material through restriction fragment analysis. In this method the amplified material is digested with restriction enzymes that recognize DNA sequences that are either present in DNA sequences derived from patients carrying an aberration in the exons or untranslated regions of the gene, or that are present in the native sequence encoding the gene product.

It is also possible to analyze a known mutation by allele specific amplification (Trends in Genetics, 12, 391-392, 1996 and Mullis et al. eds, The polymerase chain reaction, Birkhauser, Boston, Basel, Berlin, 1994, pp 1-13) Allele specific PCR for the FIIG20210A variation has been described in Thrombosis and Haemostasis 78, 1157-1163 (1997). This technique is based on the observation that under certain conditions primer elongation cannot take place when the 3' terminal nucleotide of a primer is not complementary to the template. With the use of two forward primers that differ only at their terminal 3' nucleotide it is possible to distinguish between homozygous or heterozygous individuals, for instance with respect to their FIIG20210A alleles: analysis of material from homozygous individuals will result in a positive amplification result with either one of the primers, material from heterozygous individuals will result in a positive amplification with both primers. Similar analysis can be performed for the FVL, and FXIIIV34L alleles, as well as for alleles of any other genes involved in the fibrinolysis system, the clotting system, or the complement system.

Other standard mutation analysis techniques known in the art may also be used (see, for example, Dracopoli, et al., Current Protocols in Human Genetics, John Wiley & Sons, Inc., NY). Examples of such techniques include, but are not limited to, restriction-fragment-length-polymorphism (RFLP) detection, hybridization using immobilized oligonucleotides or oligonucleotide arrays, mismatch-repair detection (MRD) (Faham and Cox Genome Res 5:474-482 (1995)), binding of MutS protein (Wagner et al. Nucl Acids Res 23:3944-3948 (1995), denaturing-gradient gel electrophoresis (DGGE), denaturing high-performance liquid chromatography (DHPLC), agarose gel or capillary-based electrophoresis, single-strand-conformation-polymorphism (SSCP) detection, RNAase cleavage at mismatched basepairs, chemical or enzymatic cleavage of heteroduplex DNA, mass spectrometry and radioactive and/or fluorescent DNA sequencing using standard procedures well known in the art.

Physiochemical analysis of the products of candidate alleles comprises immunological or physiochemical detection.

Immunological detection comprises the steps of obtaining a sample of the patient's blood, plasma, or other bodily fluid in which the gene product may or may not be present, adding a known quantity of an antibody specific to the variant gene product under condition which favor binding of the specific antibody to the variant gene product, and assessing the presence or absence of the binding of the antibody to the variant gene product. A positive test result wherein such binding is observed is indicative of the presence of the gene product, and a negative test result wherein such binding is not observed is indicative of the absence of the gene product.

For the purpose of this application, an antibody is an immunoglobulin molecule and immunologically active portions of an immunoglobulin molecule, i.e., a molecule that contain an antigen binding site which specifically binds (immunoreacts with) an antigen.

A naturally occurring antibody (e.g., IgG) includes four polypeptide chains, two heavy (H) chains and two light (L) chains inter-connected by disulfide bonds. However, the antigen-binding function of an antibody can be performed by fragments of a naturally occurring antibody. Thus, these antigen-binding fragments are also intended to be designated by the term antibody. Examples of binding fragments encompassed within the term antibody include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., Nature 341:544-6, 1989) which consists of a VH domain; (v) an isolated complementarity determining region (CDR); and (vi) an F(ab')2 fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv); Bird et al. Science 242: 423-6, 1988; and Huston et al., *Proc. Natl. Acad. Sci.* 85:5879-83, 1988) by recombinant methods. Such single chain antibodies are also included.

In one example, antibody fragments are capable of crosslinking their target antigen, e.g., bivalent fragments such as F(ab')2 fragments. Alternatively, an antibody fragment which does not itself crosslink its target antigen (e.g., a Fab fragment) can be used in conjunction with a secondary antibody which serves to crosslink the antibody fragment, thereby crosslinking the target antigen. Antibodies can be fragmented using conventional techniques and the fragments screened for utility in the same manner as described for whole antibodies. An antibody is further intended to include bispecific and chimeric molecules that specifically bind the target antigen.

"Specifically binds" as used herein with reference to an antibody, or antibody fragment, refers to the ability of an individual antibody, or fragment, to specifically immunoreact with an antigen. The binding is a non-random binding reaction between an antibody molecule and an antigenic determinant of the T cell surface molecule. The desired binding specificity is typically determined from the reference point of the ability of the antibody to differentially bind the T cell surface molecule and an unrelated antigen, and therefore distinguish between two different antigens, particularly where the two antigens have unique epitopes. An antibody that specifically binds to a particular epitope is referred to as a "specific antibody".

Physiochemical detection comprises the steps of obtaining a sample of the patient's blood, plasma, or other bodily fluid in which the gene product may or may not be present, optionally isolating the gene product from the sample by immunological or physical means, and assessing the presence or absence of the variant gene product.

In the context of the present invention, an "isolated" biological component (such as a nucleic acid molecule, polypeptide, or protein) has been substantially separated or purified away from other biological components in the cell of the organism in which the component naturally occurs (i.e. other chromosomal and extrachromosomal DNA and RNA). Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins. The term "isolated" does not require absolute purity; rather, it is intended as a relative term. Thus, for example, a substantially purified protein or nucleic acid preparation is one in which the protein or nucleic acid referred to is more pure than the protein in its natural environment within a cell or within a production reaction chamber (as appropriate). For example, a preparation of a modified protein is purified if the protein represents at least 50%, for example at least 70%, of the total protein content of the preparation. Methods for purification of proteins and nucleic acids are well known in the art. Examples of methods that can be used to purify a protein include, but are not limited to the methods disclosed in Sambrook et al. (*Molecular Cloning: A Laboratory Manual*, Cold Spring Harbor, N.Y., 1989, Ch. 17).

By "isolating the gene product from the sample by immunological means" is meant, for example, that the variant gene product may be isolated from the patient sample by means of an antibody capable of detecting both the wild-type and the variant form of the gene product (that is, an antibody directed to an epitope conserved in both the wild-type and the variant gene product, but unique to the products of that gene locus). By "isolating the gene product from the sample by physical means" is meant, that the variant gene product may be isolated from the patient sample by means of centrifugation, chromatography, electrophoresis, or other techniques known to the worker skilled in the art.

By "physiochemically assessing the presence or absence of the variant gene product" is meant the use of techniques such as protein kinetics, spectroscopy, crystallography or other techniques known to workers skilled in the art to distinguish the unique physiochemical signature of the variant gene product from that of the native or wild-type protein.

Finally, the frequency of occurrence of a particular variant within the sample population can be compared with the frequency of occurrence in the reference population and the statistical significance of any difference can be calculated by standard methods. A statistically significant difference in the frequency of occurrence between the two populations indicates that the variant is a risk factor for myocardial infarction.

Determining the Risk of Myocardial Infarction to the Individual.

The present invention further provides for methods of determining the risk for myocardial infarction to an individual and/or the propensity of an individual towards myocardial infarction. Thus, the present invention relates to a method for the detection of a plurality of defects in a multistage, multi-factorial biochemical reaction system such as the fibrinolysis system, the clotting system, or the complement system, wherein the defects are associated with an increased risk of myocardial infarction in an individual. The method comprises the steps of obtaining a suitable biological sample from the individual, analyzing for the presence of variant gene sequences, gene products of genes, or activities of gene products known to be associated with myocardial infarction, and determining the risk to the individual of myocardial infarction. The method may optionally further comprise a preliminary step of screening for suitable individuals at risk of myocardial infarction.

In one embodiment of the present invention, the variant genetic elements associated with myocardial infarction being analyzed for are one or more variant gene selected from the group of: genes encoding Factor II, Factor V, Factor XIII, or a combination thereof. In a further embodiment, the variant genetic elements associated with myocardial infarction being analyzed for are one or more variant gene selected from the group of: FIIG20210A, FVL, FXIIIV34L, or a combination thereof. In another embodiment, the variant genetic elements associated with myocardial infarction being analyzed for are two or more variant gene selected from the group of: genes encoding Factor II, Factor V, Factor XIII, or a combination thereof.

It was hitherto unrecognized that a combined carrier status of the FIIG20210A and FXIIIV34L genetic elements is a strong risk factor for myocardial infarction. With the present invention such a correlation has now been established. Therefore, in another embodiment of the present invention, the variant genetic elements associated with myocardial infarction being analyzed for are FIIG20210A and FXIIIV34L.

1. Screen for Risk Factors to Select Patients

In general, in such a preliminary screening step, if one is undertaken, individuals are selected either according to a family history of myocardial infarction, indicative of a genetic predisposition to the condition, or on the basis of an individual case study. In a typical individual case study, a patient may either present with a prior history of myocardial infarction, or global parameters may determine the interaction of several components of the clotting system. For example, the prothrombin time (PT) is a global parameter which determines the state of the exogenous clotting system and the partial thromboplastin time (aPTT) is a global parameter which determines the state of the endogenous clotting system. The prothrombin level can be measured in a human plasma sample or other suitable biological sample using techniques known in the art. Measuring prothrombin levels in a statistically sufficient number of healthy individuals can define a normal value.

If a positive family history is recorded, or a positive finding is obtained from a personal history or a global parameter such as PT or aPTT, individuals parameters can be analysed to discover the underlying genetic basis for the condition.

2. Obtaining a Suitable Biological Sample

A suitable biological sample is obtained from the individual under study in order to carry out the analysis. As described above, biological samples obtained from a subject may contain genomic DNA, RNA, or protein, and can be a blood or blood plasma sample containing a protein of interest or a blood or blood plasma sample, urine, saliva, tissue biopsy, surgical specimen, fine needle aspirates, amniocentesis samples, or other material comprising the patient's genomic DNA. Methods for obtaining suitable biological samples are known in the art.

3. Analysis

Suitable methods of analysis comprise physiochemical analysis such as enzyme assay, an immunoassay to determine the presence of a variant gene product, or a nucleic acid analysis to determine the presence of a variant gene sequence. Such methods are described in detail above.

The physiochemical analysis comprises individual parameters, each of which determines the presence or absence of only an individual genetic product, such as variants of Factors II, V, or XIII, or other components involved in the fibrinolysis system, the clotting system, or the complement system. For example, the presence of the gene product of the FXIIIV34L allele can be determined by reaction with an antibody which specifically binds to the epitope comprising the valine to leucine substitution at amino acid position 34.

The nucleic acid analysis comprises assessing individual parameter, each of which determines the presence or absence of only an individual genetic element, such as FVL, FIIG20210A or FXIIIV34L alleles, or any other genetic element involved in the fibrinolysis system, the clotting system, or the complement system. For example, the presence of the FVL allele can be determined by the use of sequence-specific oligonucleotides.

In Example 1, the FII, FV, and FXIII genes were analyzed as candidate genes in a search for genetic elements that may contribute to elevated risk of myocardial infarction. FII is encoded by a 21-kb-long gene localized on chromosome 11, position 11p11-q12. The gene is organized in 14 exons, of which exon 1 comprises the 5' untranslated (UT) region and exon 14 comprises the 3'-UT region. The nucleotide sequence of the FII gene, its flanking sequences as well as the position of the various exons has been described previously (Biochemistry 26, 6165-6177, 1987). The G20210A sequence variation is located at the last position of the 3'-UT at or near the cleavage site in the mRNA precursor to which poly A is added. Three conserved sequences in mRNA precursors, located in the vicinity of this site, are required for cleavage and polyadenylation: the AAUAAA sequence, the nucleotide to which poly A is added, and the region downstream of this nucleotide. Generally, the nucleotide to which poly A is added is an A, mostly preceded by a C. As a consequence of the G to A transition at position 20210, a CA dinucleotide (rather than a GA dinucleotide) has been introduced at or near the cleavage and polyadenylation site.

FV and FXIII are encoded by genes whose nucleotide sequence, flanking sequences, and position of the various exons have been described previously. Genetic analysis of the candidate genes comprises obtaining from the patient a biological sample, selectively amplifying from said sample of nucleic acid coding regions or other regulatory elements of the candidate genes comprising the genetic aberration, and analyzing the sequence for the presence of signature substitutions indicative of the gene variant of interest. Biological samples are those containing genomic DNA, cDNA, RNA, or protein obtained from the cells of a subject, such as those present in peripheral blood, urine, saliva, tissue biopsy, surgical specimen, fine needle aspirates, amniocentesis samples and autopsy material.

As is illustrated in example 1, the G20210A mutation in the FII gene, combined with the V34L mutation in the FXIII gene, has been demonstrated to be present in a group of patients exhibiting a risk for myocardial infarction without the cause thereof having been previously determined. Example 1, which illustrates the general use of the methods for the detection of mutations indicative of an elevated risk for myocardial infarction, is provided for illustrative purposes only.

The study in Example 1 shows that the presence of sequence variation G20210A in the FII gene, combined with the sequence variation V34L in the FXIII gene, is a risk factor for myocardial infarction.

4. Determining Risk of Myocardial Infarction

Once the genetic material from the patient's sample has been analyzed for the presence of the sequence variation in the target gene, or the biological material from the patient's sample has been analyzed for the presence of the variant product of the target gene, the risk for myocardial infarction can be determined on the basis of the risk established in a case-control study such as, for example, the Newfoundland study of Example 1.

Kit for the Detection of Risk Factors Associated with Myocardial Infarction

Kits for the detection of risk factors associated with myocardial infarction may be kits for the genetic, immunological or physiochemical detection of risk factors associated with myocardial infarction.

Kits for the genetic detection of risk factors associated with myocardial infarction comprise oligonucleotides specific to the variant region of the alleles of interest or to sequence flanking the variant region, and optionally buffers, nucleotides, enzymes such as polymerases, ligases or endonucleases as appropriate to the specific method of genetic analysis known in the art, and other reagent useful in performing such analysis.

Kits for the immunological detection of risk factors associated with myocardial infarction comprise primary antibodies (monoclonal, polyclonal or purified) specific to the variant epitopes of the gene products of interest, and optionally buffers, membranes, secondary antibodies, and preferably labeled secondary antibodies specific to the primary antibodies, and other reagent useful in performing such analysis.

Kits for the physiochemical detection of risk factors associated with myocardial infarction comprise electrophoresis buffers, centrifugation buffers, substrates specific to the variant gene products, and preferably chromogenic substrates, and other reagent useful in performing such analysis.

To gain a better understanding of the invention described herein, the following examples are set forth. It should be understood that these examples are for illustrative purposes only. Therefore, they should not limit the scope of this invention in any way.

EXAMPLES

Example 1

Subjects, Materials and Methods

Subjects:

Blood samples were collected from 500 consecutive myocardial infarction patients and 500 normal controls of the genetically isolated Newfoundland population. The population consists mainly of descendants of English and Irish settlers who arrived in the 18$^{th}$ and 19$^{th}$ centuries. The geographic and social isolation of the island has ensured very little inward migration for several hundred years, and thus has lead to a small population (530,000 individuals) with a relatively homogenous genetic background, ideal for the study of complex multifactorial diseases such as myocardial infarction.

Patients categorized in the myocardial infarction group represented those presenting to the emergency department or within one of the Health Care Corporation of St. John's hospitals with symptoms and biochemical evidence suggestive of myocardial infarction. Only patients with cardiac Troponin I values greater than 2.0 μg/L (Axsym, Abbott Diagnostics) or greater than 0.5 μg/L (Access II, Beckman-Coulter Corp.) were used in this group. Control subjects were selected from consecutive individuals without prior history of myocardial infarction or thrombosis presenting to the emergency department for trauma, accidental injury, or other non-cardiac and non-thrombotic related events. Discarded blood samples collected for complete blood count were used for DNA extraction and analysis. Ethics approval for this study was granted by the Human Investigations Committee of Memorial University and by the Health Care Corporation of St. John's.

Genotyping of FIIG20210A, FVL, and FXIIIV34L.

Genomic DNA was isolated from the peripheral blood using standard methods (Miller S. A., Dykes D. D., Polensky H. F., A simple salting out procedure for extracting DNA from human nucleated cells. Nucleic Acid Research 1988; 16(3): 1215). Genotyping of the FVL, FIIG20210A, and FXIIIV34L was performed by PCR amplification of each of the target alleles from genomic DNA followed by restriction digestion with each of corresponding enzymes MnlI, HindIII and DdeI respectively, as previously described (Linfert D. R., Rezuke W. N., Tsongalis G. J., Rapid multiplex analysis for the factor V Leiden and prothrombin G20210A mutations associated with hereditary thrombophilia. Conn. Med. 1998: 62(9): 519-25). The digested PCR products were separated by electrophoresis in 10% polyacrylamide gels and visualized by staining with ethidium bromide.

Prevalence Determination and Association Study:

The prevalence of each gene variant was calculated by counting the total carrier frequency including heterozygotes and homozygotes. The allele frequencies were determined by gene counting. Pearson Chi Square statistical analysis was performed using SPSS v10.0 to test the association between genotypes and the prevalence of myocardial infarction. Odds ratios (OR) were calculated as a measure of the relative risk for myocardial infarction and were given with 95% confidence intervals.

Analysis of Gene-Gene Interaction:

Gene-gene interactions were determined, first by comparing the prevalence of combined carrier for two of the three gene variants in patients and controls; and second by analysis of the distribution of one chosen gene variant in sub-grouped patients and controls who carry another gene variant as genetic background.

Results

Genotyping FIIG20210A, FVL, and FXIIIV34L.

The genotype distributions, carrier frequencies, and allele frequencies of FIIG20210A, FVL, and FXIIIV34L in both the myocardial infarction patient and the control populations are given in Table 1 below.

TABLE 1 distributions of genotypes, and carrier and allele frequencies of FIIG20210A, FVL and FXIII-A V34L in MI patient and normal control populations. (MI: myocardial infarction, NC: normal control, OR: odds ratio) The FIIG20210A allele was detected in 3.2% of patients which was significantly higher than the 1% observed in controls (OR 3.3, 95% CI 2.6–4.0; P = 0.015).

|  | Genotype | MI (n = 500) | NC (n = 500) | OR | P value |
|---|---|---|---|---|---|
| FIIG20210A | G/G | 484 (96.8%) | 495 (99.0%) | | |
|  | G/A | 16 (3.2%) | 5 (1.0%) | | |
|  | A/A | 0 (0%) | 0 (0%) | | |
| Carrier F. |  | 3.2% | 1.0% | 3.3 | 0.015 |
| Allele F. |  | 1.6% | 0.5% | | |
| FVL(R506Q) | R/R | 477 (95.4%) | 477 (95.4%) | | |
|  | R/Q | 23 (4.6%) | 23 (4.6%) | | |
|  | Q/Q | 0 (0%) | 0 (0%) | | |
| Carrier F. |  | 4.6% | 4.6% | 1.00 | NS |
| Allele F. |  | 2.3% | 2.3% | | |
| FXIIIV34L | V/V | 265 (53.0%) | 261 (52.2%) | | |
|  | V/L | 193 (38.6%) | 207 (41.4%) | | |
|  | L/L | 42 (8.4%) | 32 (6.4%) | | |
| Carrier F. |  | 47.0% | 47.8% | 0.97 | NS |
| Allele F. |  | 27.7% | 27.1% | | |

An identical prevalence of FVL was observed in both patient and control populations (4.6% vs. 4.6%). No homozygotes for either FIIG20210A or FVL allele were found in either population. In both patient and control populations, FXIIIV34L had similar prevalence (47.0% vs. 47.8%) and allele frequency (27.7% vs. 27.1%). The prevalence of homozygous V34L was higher in patients compared with controls (8.4% vs. 6.4%), but the difference did not reach statistical significance. It is to be understood that, because the statistical significance of the prevalence of a genetic element as it relates to myocardial infarction risk is dependent on the sample size, an increase in the sample size will conclusively determine said statistical significance.

The distribution of the three gene variations was further analyzed by sub-grouping patients and controls according to age, as shown in Table 2 below.

TABLE 2 distribution of genotypes among MI patients with different onset ages and compared with age-matched normal controls. Myocardial infarction patients were divided into those with an early age of onset (less than 50 years) and those with a later age of onset (greater than 50 years).

|  | MI | NC | OR | P |
| --- | --- | --- | --- | --- |
| FII G20210A Carriers | 16/500 (3.2%) | 5/500 (1%) | 3.3 | 0.015 |
| Age ≦50 Y | 2/46 (4.3%) | 3.373 (0.8%) | 5.6 | 0.04 |
| Age >50 Y | 14/454 (3.1%) | 2/127 (1.6%) | 2.0 | NS |
| FVL Carriers | 23/500 (4.6%) | 23/500 (4.6%) | 1.0 | NS |
| Age ≦50 Y | 6/46 (13.0%) | 18/373 (4.8%) | 3.0 | 0.007 |
| Age >50 Y | 17/454 (3.8%) | 5/127 (3.9%) | 1.0 | NS |
| FXIII-V34LCarriers | 235/500 (47.0%) | 239/500 (47.8%) | 1.0 | NS |
| Age ≦50 Y | 19/46 (41.3%) | 176/373 (47.2%) | 0.8 | NS |
| Age >50 Y | 216 (47.6%) | 63/127 (49.6%) | 0.9 | NS |

The control population was also divided into the two corresponding age groups. Interestingly, a disequilibrium distribution of the FVL allele was observed in the early onset patient group. The FVL allele was detected in 13.0% of patients with early age of onset, which was significantly higher than the 3.8% in patients with a later age of onset (OR: 3.9, 95% CI 3.3-4.4; P=0.004) and the 4.8% in the age matched controls (OR: 3.0, 95% CI 2.2-3.7; P=0.007). The prevalence of FIIG20210A was also significantly higher in the early onset group of myocardial infarction (4.3%) compared to the controls under age 50 (0.8%). Although, the prevalence of FIIG20210A was slightly higher in the early onset group compared to the later onset group, this difference did not achieve statistical significance. The FXIIIV34L showed a slight but statistically insignificant difference in prevalence between the patients with early and later onset age.

Gene-Gene Interactions:

Interaction between FXIIIV34L and FIIG20210A was first analyzed by comparing the prevalence of combined carriers (individuals carrying both FIIG20210A and FXIIIV34L) in the total patient and control populations with their corresponding theoretical prevalence of combined carriers.

Using carrier frequencies described in Table 1, the theoretical prevalence for combined carriers of FIIG20210A and FXIIIV34L is 1.5% (47.0%×3.2%) in myocardial infarction patients and 0.48% (47.8%×1%) in controls (FIG. 1a).

The observed prevalence of combined carriers in the myocardial infarction patient population (2.4%; 12 of 500) was 1.6-fold higher than its theoretic prevalence (1.5%), and in normal control population (0.2%; 1 of 500) was 2.4-fold lower than its theoretic expected prevalence (0.48%). The observed prevalence of combined carriers was 12-fold higher in myocardial infarction patient compared with the control population (P=0.002).

Figure 2A:
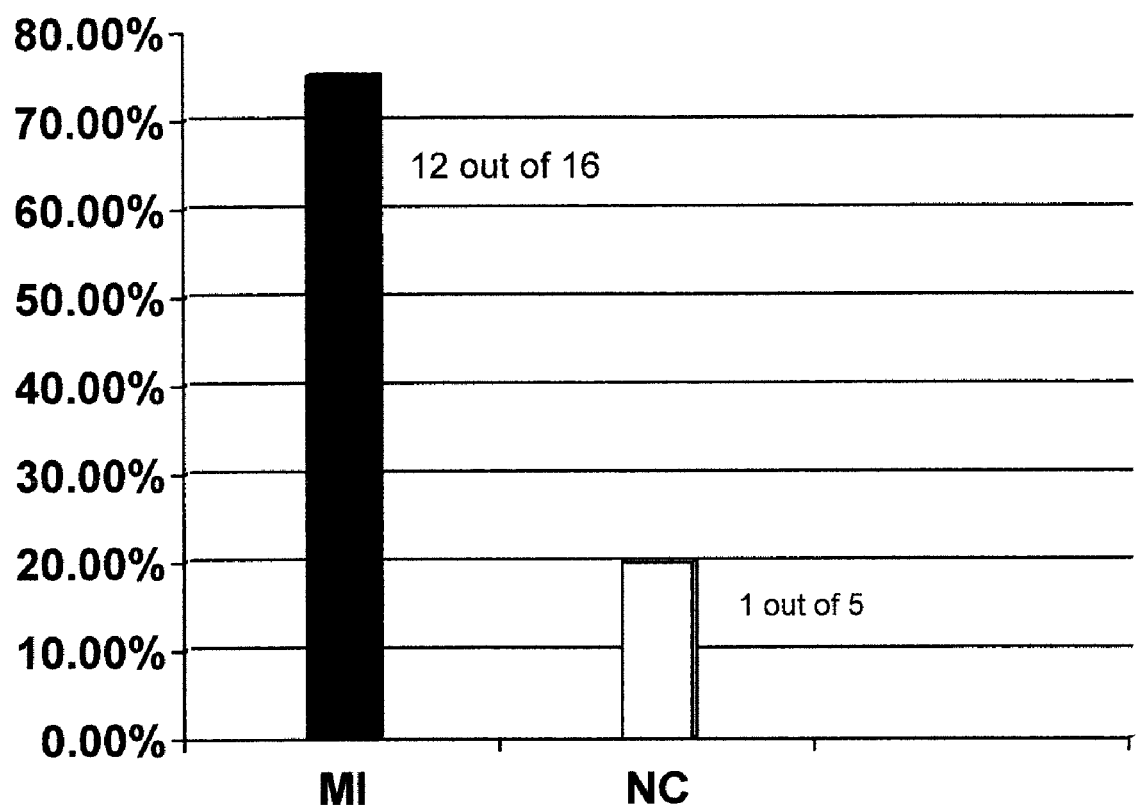
FIG. 2 shows the prevalence of (a) FXIIIV34L in MI patients and normal controls who carry the FIIG20210A allele, and (b) FXIIIV34L in MI patients and normal controls who carry the FVL allele, as described in Example 1 (MI=500 individuals, control=500 individuals)
Figure 2B:
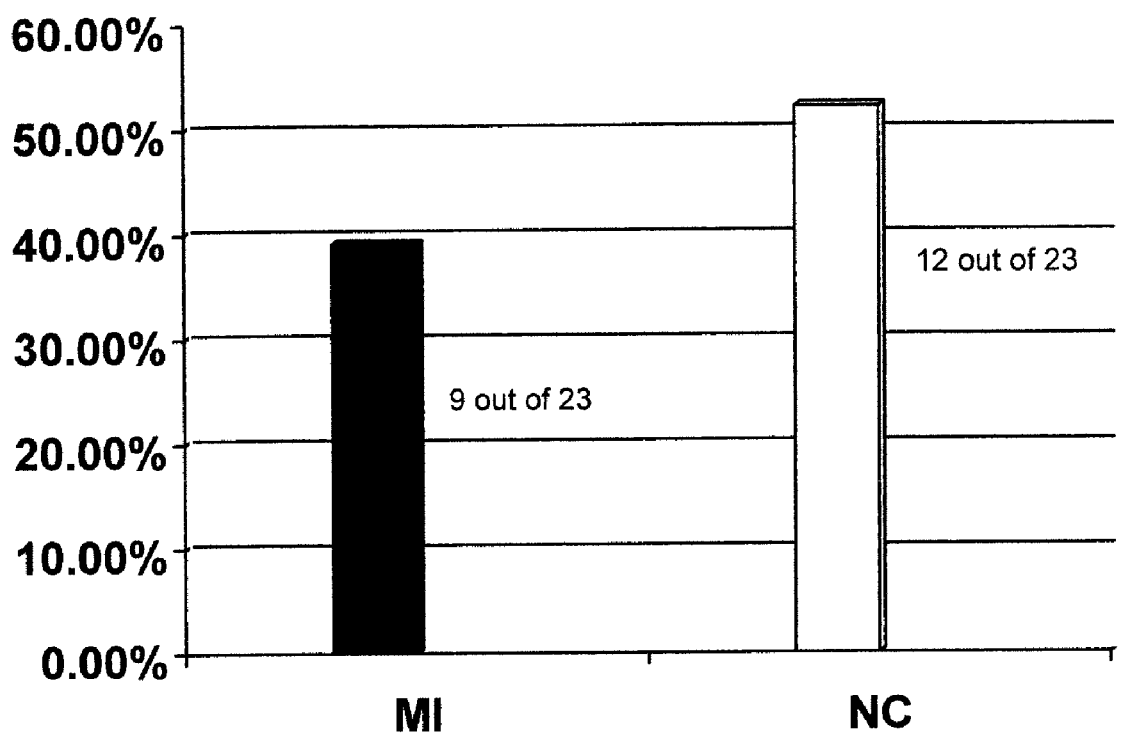

The interaction between the FIIG20210A and the FXIIIV34L was further examined by analysis of the distribution of FXIIIV34L in sub-grouped patients and controls who carry FIIG20210A as a genetic background. Although the FXIIIV34L showed an almost equal distribution in our myocardial infarction patient and control populations, FXIIIV34L alleles were detected in 75.0% (12 of 16) patients with a genetic background of FIIG20210A but only in 20.0% (1 of 5) of controls with the same genetic background (OR 3.7. 95% CI 2.4-5.1; P=0.013) (FIG. 2: (a) Prevalence of FXIIIV34L in MI patients and normal controls who carry the Fiig20210A allele (b) Prevalence of FXIIIV34L in MI patients and normal controls who carry the FVL allele).

Of 13 combined carriers of FIIG20210A and FXIIIV34L identified from the studied population (500 patients and 500 controls), 12 subjects (92.3%) belonged to the myocardial infarction patient population but only 1 (0.7%) from the control population. The co-existence of these two gene variants imparts a strong predisposition for myocardial infarction with high penetrance.

Figure 1B:
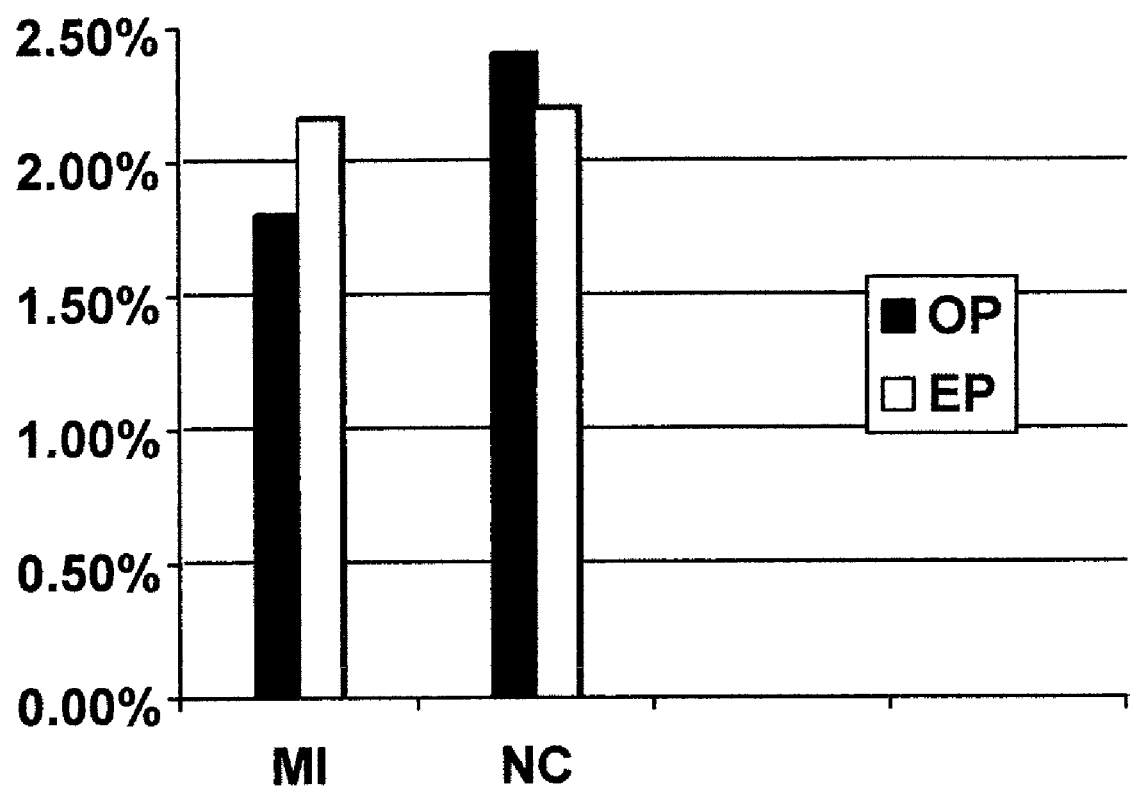

The prevalence of combined carriers of FVL and FXIIIV34L were similar in both myocardial infarction patient (12 of 500, 2.4%) and control (9 of 500, 1.8%) groups and was consistent with their expected frequencies (2.16% in patients and 2.2% in controls; FIG. 1b). We further analyzed the prevalence of FXIIIV34L in patients and controls who carry the FVL allele as a genetic background. The prevalence of FXIIIV34L was slightly higher in the sub-grouped controls (13 of 23, 56.52%) than in the sub-grouped patients (9 of 23. 39.1%) but the difference was not statistically significant.

There were no combined carriers of FIIG20210A and FVL in the myocardial infarction patient or control populations. This is expected considering a calculated expected frequency of combined carriers of 0.13% in myocardial infarction patients and 0.01% in normal controls, respectively.

FIG. 1(a) comparison of the expected and observed prevalence of combined carrier for FIIG20210A and FXIIIV34L among MI patients and controls; (b) comparison of the expected and observed prevalence of combined carrier for FVL and FXIIIV34L among MI patients and controls. OP: observed prevalence; EP: expected prevalence (prevalence of FIIG20210A×prevalence of FXIIIV34L).

Example 2

Subjects, Materials and Methods

Blood samples were collected from 230 additional patients with MI and 79 additional normal controls, using the methods and materials set out in Example 1. The cumulative summary of the results based total 730 patients with MI and 579 normal controls are given in the following tables and figures:

Results

Genotyping FIIG20210A, FVL and FXIII-A V34L

The genotype distributions, carrier frequencies, and allele frequencies of FII G20210A, FVL, and FXIII-A L34 in both the MI patient and the control populations are given in Table 3 below.

TABLE 3 distributions of genotypes, and carrier and allele frequencies of FIIG20210A,
FVL and FXIII-A V34L in MI patient and normal control populations. (MI: myocardial
infarction, NC: normal control, OR: odds ratio).

|  | Genotype | MI (n = 730) | NC (n = 579) | OR (95% CI) | P value |
|---|---|---|---|---|---|
| FIIG20210A | G/G | 710 (97.3%) | 572 (98.8%) | | |
| | G/A | 20 (2.7%) | 7 (1.2%) | | |
| | A/A | 0 (0%) | 0 (0%) | | |
| Carrier F. | | 2.7% | 1.2% | 2.302(0.967, 5.482) | 0.053 |
| Allele F. | | 1.4% | 0.6% | | |
| FVL(R506Q) | R/R | 693 (94.9%) | 553 (95.5%) | | |
| | R/Q | 38 (5.2%) | 26 (4.5%) | | |
| | Q/Q | 0 (0%) | 0 (0%) | | |
| Carrier F. | | 5.2% | 4.5% | 1.16(0.694, 1.926) | 0.577 |
| Allele F. | | 2.6% | 2.3% | | |
| FXIIIV34L | V/V | 391 (53.6%) | 303 (52.3%) | | |
| | V/L | 228 (31.2%) | 207 (40.8%) | | |
| | L/L | 57 (7.8%) | 32 (6.9%) | | |
| Carrier F. | | 39% | 41.3% | 0.948(0.772–1.159) | 0.592 |
| Allele F. | | 23.4% | 23.4% | | |

The FIIG20210A allele was detected in 2.7% of patients, which was higher than the 1.2% observed in controls (OR 2.26, 95% CI 0.95-5.5.0, P=0.059). Prevalence of FVL was observed in 5.2% patient and 4.5% control populations. No homozygotes for either the FIIG20210A or FVL alleles were found in either population. In both patient and control populations, the FXIIIV34L allele had similar prevalence (39.0% vs. 41.3%) and allele frequency (23.4% vs. 23.4%). The prevalence of homozygosity for the FXIIIV34L allele was higher in patients compared with controls (7.8% vs. 6.9%), but the difference did not reach statistical significance.

Gene-Gene Interaction.

The observed prevalence of combined carrier in the MI patient population (1.92%, 14 of 730) was 1.8-fold higher than it's theoretical prevalence (1.1%), and in normal control population (0.17%; 1 of 79) was 2.9-fold lower than its theoretic expected prevalence (0.5%). The relative risk for the combined carriers to development MI is 11.3.

Figure 4:
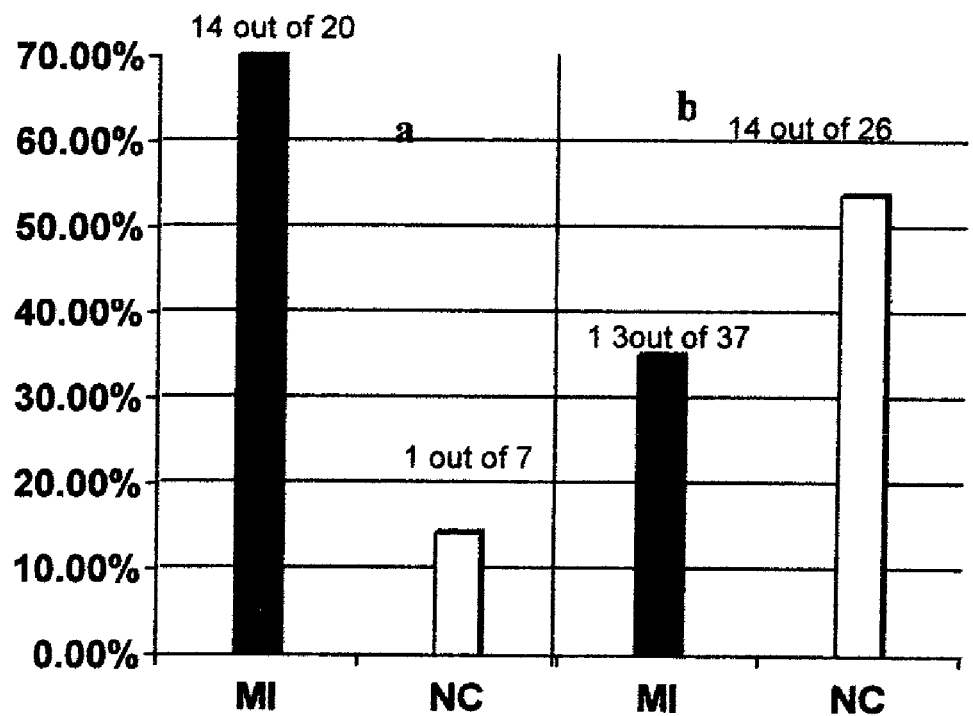
FIG. 4 shows the prevalence of (a) FXIIIV34L in MI patients and normal controls who carry the FIIG20210A allele and (b) FXIIIV34L in MI patients and normal controls who carry the FVL allele, as described in Example 2 (MI=730 individuals, control=579 individuals).

The interaction between the FII-G20210A and the FXIIIV34L alleles was further examined by analysis of the distribution of the FXIIIV34L allele in sub-grouped patients and controls who carry the FII-G20210A allele as a genetic background. Although the FXIIIV34L allele showed an almost equal distribution in our MI patient (39%) and control populations (41%), it was detected in 70% (14 of 20) patients with a genetic background of the FII-G20210A allele but only in 14.3% (1 of 7) of controls with the same genetic background (OR 4.9, 95% CI 0.8-30.8, P=0.011) (FIG. 4: Prevalence of the FXIIIV34L allele in MI patients and normal controls (NC) who carry the FII-G20210A allele (a) and FVL (b) (MI=730, NC=579)).

Of 15 combined carriers of the FII-G20210A and FXIIIV34L alleles identified from the studied population (730 patients and 579 controls), 14 subjects (93.3%) had MI. The co-existence of these two gene variants imparts a strong predisposition for MI with high penetrance.

Figure 3:
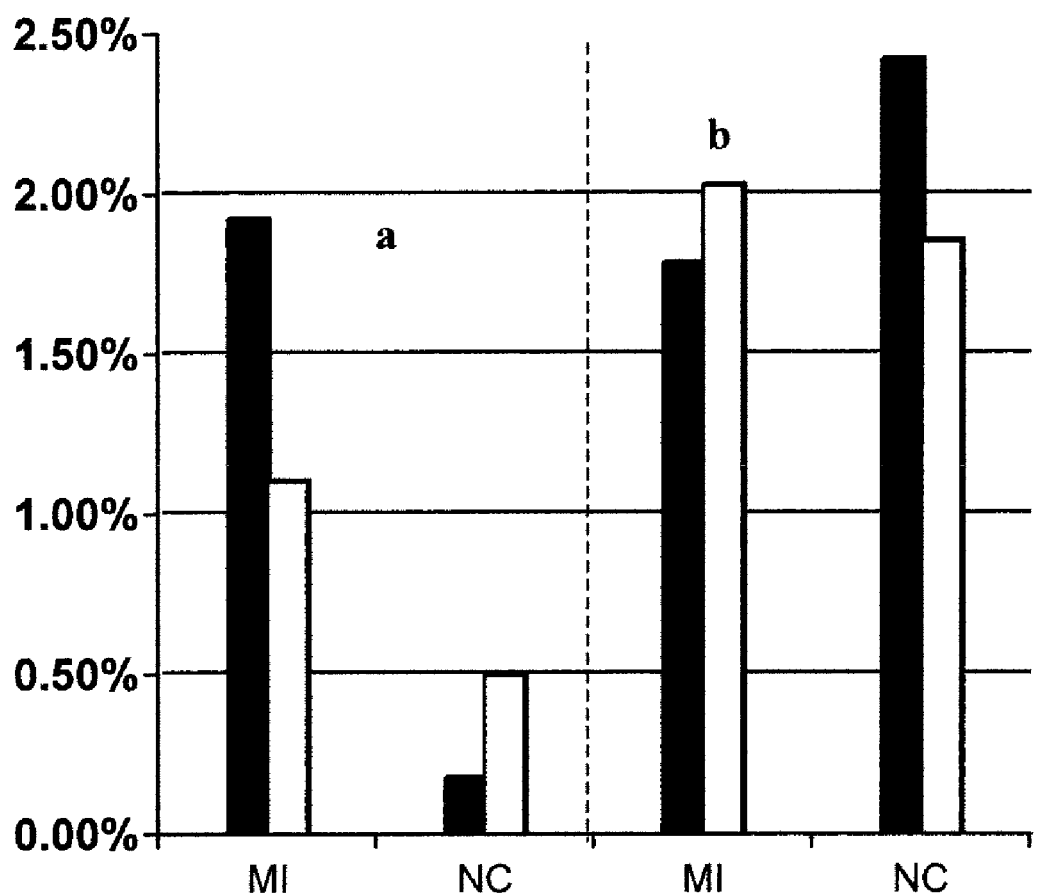
FIG. 3 shows a comparison between expected and observed prevalence of combined carriers of mutations in myocardial infarction as described in Example 2 (MI=730 individuals, control 579 individuals)

The prevalence of combined carriers of FVL and the FXIIIV34L allele was 1.78% (13 of 730) in MI patients, which is lower than its expected frequency, 2.03%. While, the prevalence of combined carriers in healthy controls was 2.42% in control groups (14 of 579), which is higher than its expected prevalence, 1.85% (FIG. 3: Comparison between the expected and observed prevalence of combined carriers of mutations in MI patients and controls. (MI=730, NC=579). (a) Comparison of the expected and observed prevalence of combined carrier for the FII-G20210A+FXIIIV34L alleles in MI patients and control subjects, respectively. (b) Comparison between the expected and observed prevalence of combined carrier for FVL+FXIIIV34L alleles in MI patients and control subjects, respectively. Filled bar (■) represents the observed prevalence of combined carriers. Empty bar (□) represents the expected prevalence of combined carriers.). However, all of these differences did not reach statistical significance.

The prevalence of the FXIIIV34L allele in patients and controls who carry the FVL allele as a genetic background was further analyzed. The prevalence of the FXIIIV34L allele was higher in the sub-grouped controls (14 of 26, 53.85%) than in the sub-grouped patients (13 of 37, 35.14%) but the difference was not statistically significant.

There was only one combined carrier of the FII-G20210A allele and FVL identified from each of the MI patient group and control populations. This is expected considering a calculated expected frequency of combined carriers of 0.13% in MI patients and 0.01% in normal controls, respectively.

TABLE 4

Distribution of genotypes among MI patients with different onset ages and compared with age-matched normal controls (NC).

|  | MI | NC | OR (95% CI) | P |
|---|---|---|---|---|
| FII-G20210A Carriers | 20/732 (2.73%) | 5/579 (0.86%) | 3.164 (1.180, 8.481) | 0.016 |
| Age ≦50 Y | 2/92 (2.17%) | 3/423 (0.71%) | 3.065 (0.505, 18.606) | 0.201 |
| Age >50 Y | 18/640 (2.81%) | 2/156 (1.28%) | 2.194 (0.504, 9.554) | 0.283 |

TABLE 4-continued

Distribution of genotypes among MI patients with different onset ages and compared with age-matched normal controls (NC).

|  | MI | NC | OR (95% CI) | P |
|---|---|---|---|---|
| FVL Carriers | 38/732 (5.19%) | 26/579 (4.49%) | 1.156 (0.694, 1.926) | 0.577 |
| Age ≦50 Y | 8/92 (8.70%) | 20/423 (4.73%) | 1.839 (0.786, 4.304) | 0.155 |
| Age >50 Y | 30/640 (4.69%) | 6/156 (3.85%) | 1.219 (0.499, 2.979) | 0.664 |
| FXIII-V34L carriers | 341/732 (46.58%) | 277/579 (47.84%) | 0.974 (0.803, 1.180) | 0.786 |
| Age ≦50 Y | 43/92 (46.74%) | 199/423 (47.04%) | 0.994 (0.666, 1.481) | 0.974 |
| Age >50 Y | 298/640 (46.56%) | 78/156 (50.0%) | 0.931 (0.687, 1.263) | 0.647 |

TABLE 5

Comparison of genotypes distribution in different genders among MI patients normal controls

|  | Males | Females | OR (95% CI) | P |
|---|---|---|---|---|
| FII-G20210A |  |  |  |  |
| MI | 9/353 (2.55%) | 10/339 (2.95%) | 0.864 (0.347, 2.153) | 0.754 |
| NC | 5/255 (1.96%) | 2/324 (0.62%) | 3.176 (0.611, 16.507) | 0.147 |
| FVL |  |  |  |  |
| MI | 26/353 (7.37%) | 10/339 (2.95%) | 2.497 (1.186, 5.256) | 0.013 |
| NC | 10/255 (3.92%) | 16/324 (4.94%) | 0.794 (0.354, 1.780) | 0.575 |
| FXIIIV34L |  |  |  |  |
| MI | 201/353 (56.94%) | 120/339 (35.40%) | 1.609 (1.227, 2.109) | 0.001 |
| NC | 119/255 (46.67%) | 126/324 (38.89%) | 1.200 (0.889, 1.619) | 0.233 |

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A method of determining an increased risk for myocardial infarction in a human individual, comprising determining in a biological sample obtained from said human individual, the presence of a combination of two or more coagulation factor variants, said combination comprising a variant of Factor II in combination with a variant of Factor XIII wherein said combination of two or more coagulation factor variants is FIIG20210A in combination with FXIIIV34L and wherein the presence of said combination of two or more coagulation factor variants is indicative of an increased risk for myocardial infarction in said human individual.

2. The method according to claim 1, wherein determining the presence of said combination of two or more coagulation factor variants comprises detecting the presence in said sample of a nucleotide sequence corresponding to the variant of Factor II, and a nucleotide sequence corresponding to the variant of Factor XIII.

3. The method according to claim 2, wherein said detecting comprises the step of amplifying each of said nucleotide sequences by polymerase chain reaction (PCR).

4. The method according to claim 2, wherein said detecting comprises direct sequence analysis of the nucleotide sequences, restriction fragment analysis of said nucleotide sequences, allele specific amplification, or hybridization screening.

5. The method according to claim 2, wherein said detecting comprises amplifying each of said nucleotide sequences by PCR to generate corresponding PCR products, and submitting each of said PCR products to restriction fragment analysis.

6. The method according to claim 1, wherein said variant of Factor II comprises the sequence as set forth in SEQ ID NO:1.

7. The method according to claim 1, wherein said variant of Factor XIII comprises the sequence as set forth in SEQ ID NO:7.

8. A method of determining an increased predisposition for myocardial infarction in a human individual, comprising:
  determining in a biological sample obtained from said human individual, the co-existence of two coagulation factor variants wherein the variants are FIIG20210A and FXIIIV34L,
  wherein the co-existence of the two variants in said human individual is indicative of an increased predisposition for myocardial infarction.

9. The method according to claim 1, further comprising determining in the sample the presence of a variant of Factor V, wherein the variant of Factor V is Factor V Leiden (FVL-R506Q).

* * * * *

UNITED STATES PATENT AND TRADEMARK OFFICE
CERTIFICATE OF CORRECTION

PATENT NO.          : 7,785,788 B2                                           Page 1 of 1
APPLICATION NO.     : 11/428829
DATED               : August 31, 2010
INVENTOR(S)         : Ya-Gang Xie It is certified that error appears in the above-identified patent and that said Letters Patent is hereby corrected as shown below:

Title Page, item "(73) Assignee: New Lab Clinical Research Inc., St. John's (CA)"

should read --(73) Assignee: Newlab Clinical Research Inc., St. John's (CA).--

Signed and Sealed this

Twenty-third Day of November, 2010

David J. Kappos
*Director of the United States Patent and Trademark Office*

SEQUENCE LISTING

```
<160> NUMBER OF SEQ ID NOS: 9

<210> SEQ ID NO 1
<211> LENGTH: 1086
<212> TYPE: DNA
<213> ORGANISM: Homo Sapiens

<400> SEQUENCE: 1
ctcaccagct gtgtctcgtg aaggggcgtg gctgggctat gagctatgct cctgagcaca      60
gacggctgtt ctctttcaag gttacaagcc tgatgaaggg aaacgagggg atgcctgtga     120
aggtgacagt gggggaccct ttgtcatgaa ggtaagcttc tctaaagccc agggcctggt     180
gaacacatct tctgggggtg gggagaaact ctagtatcta gaaacagttg cctggcaggg     240
gaatactgat gtgaccttga acttgactct attggaaacc tcatctttct tcttcagagc     300 cccttttaaca accgctggta tcaaatgggc atcgtctcat ggggtgaagg ctgtgaccgg     360
gatgggaaat atggcttcta cacacatgtg ttccgcctga agaagtggat acagaaggtc     420
attgatcagt ttggagagta gggggccact catattctgg gctcctggaa ccaatcccgt     480
gaaagaatta tttttgtgtt tctaaaacta tggttcccaa taaaagtgac tctcagcaag     540
cctcaatgct cccagtgcta ttcatgggca gctctctggg ctaggaagag ccagtaatac     600
```

-continued

```
tactggataa agaagactta agaatccacc acctggtgca cgctggtagt ccgagcactc      660
gggaggctga ggtgggagga tcgcttgagc ccaggaggtg gaggctgcag tgagccactg      720 cacccccagcc tgggtgacag agtgagaccc tgtcccaaaa gaatccacta tctatcttca     780
gagcagggcc aggtgagagg aaagatggca ggttgaattt acaggcatta aagatgttcc      840
accctctggg ttttaatgga ttatctcatt taatcctcac aagaggtagg tgagtaaact      900
gagatttgga gaagtacctt gtccaaagtc acatggctaa gaaagctcaa agtaggactt      960
caaatataga aaatattgag tgaggacggt gcttttttag ttaactccct acatcttccc     1020
ttgtatcatt aaaatgatat cagatcaggt agggcatggt ggctcacacc tgtaatctca     1080
gcaatt                                                                1086

<210> SEQ ID NO 2
<211> LENGTH: 20
<212> TYPE: DNA
<213> ORGANISM: Artificial Sequence
<220> FEATURE:
<223> OTHER INFORMATION: Nucleotide primer sequence

<400> SEQUENCE: 2
tctagaaaca gttgcctggc                                                   20

<210> SEQ ID NO 3
<211> LENGTH: 22
<212> TYPE: DNA
<213> ORGANISM: Artificial Sequence
<220> FEATURE:
<223> OTHER INFORMATION: Nucleotide primer sequence

<400> SEQUENCE: 3
atagcactgg gagcattgaa gc                                                22

<210> SEQ ID NO 4
<211> LENGTH: 480
<212> TYPE: DNA
<213> ORGANISM: Homo Sapiens

<400> SEQUENCE: 4
gcaaatgaaa acaattttga atatattttc tttcaggcag gaacaacacc atgatcagag       60
cagttcaacc aggggaaacc tatacttata agtggaacat cttagagttt gatgaaccca      120
cagaaaatga tgcccagtgc ttaacaagac catactacag tgacgtggac atcatgagag      180
acatcgcctc tgggctaata ggactacttc taatctgtaa gagcagatcc ctggacaggc      240
aaggaataca ggtattttgt ccttgaagta acctttcaga aattctgaga atttcttctg      300
gctagaacat gttaggtctc ctggctaaat aatggggcat ttccttcaag agaacagtaa      360
ttgtcaagta gtcctttta gcaccagtgt gataacattt attcttttt ttttttgtc        420 ttgtctattt ttatcagtac catcactgcc gaaggcaagt ctagagtgtg ataacatatt      480

<210> SEQ ID NO 5
<211> LENGTH: 21
<212> TYPE: DNA
<213> ORGANISM: Artificial Sequence
<220> FEATURE:
<223> OTHER INFORMATION: Nucleotide primer sequence

<400> SEQUENCE: 5
acccacagaa aatgatgccc a                                                 21
```

-continued

```
<210> SEQ ID NO 6
<211> LENGTH: 21
<212> TYPE: DNA
<213> ORGANISM: Artificial Sequence
<220> FEATURE:
<223> OTHER INFORMATION: Nucleotide primer sequence

<400> SEQUENCE: 6
tgccccatta tttagccagg a                                              21

<210> SEQ ID NO 7
<211> LENGTH: 653
<212> TYPE: DNA
<213> ORGANISM: Homo Sapiens

<400> SEQUENCE: 7
ttccatatgt tttgacacat acaaaaatct ccccaagatc cttggggaac tgtattccat    60
cattagacta atccttgctg ccacttctca gttttttattt atgcaaacgg caaaatgtgt   120
tgctcaagtg ctatcacaca cagatatatc tgtttctcta ttttggaatc cttgtctcaa   180
atgttactca ctttacatgc cttttctgtt gtcttctttt ttttttttttt ctgaaggacc   240 ttgtaaagtc aaaaatgtca gaaacttcca ggaccgcctt tggaggcaga agagcagttc   300
cacccaataa ctctaatgca gcggaagatg acctgcccac agtggagctt cagggcttgg   360
tgccccgggg cgtcaacctg caaggtatga gcataccccc cttccccacc actctgggtc   420
caggcacagc cgggccctgg cccctcttcc ctgcaggtaa acatcctctg tctccactgg   480
ggttcccaca aaaggaagcc ccctgccaat ctctggtttt ataaaggaag aaagcaaaag   540
ctttctttta agtggtgaaa gcaccgaaga cccagagcct tgtcccagtt ctgcccctta   600
ctgaccttgt aacctcagag aagttgcttt gtctttctgc ctctcaacta ttt          653

<210> SEQ ID NO 8
<211> LENGTH: 21
<212> TYPE: DNA
<213> ORGANISM: Artificial Sequence
<220> FEATURE:
<223> OTHER INFORMATION: Nucleotide primer sequence

<400> SEQUENCE: 8
catgcctttt ctgttgtctt c                                              21

<210> SEQ ID NO 9
<211> LENGTH: 30
<212> TYPE: DNA
<213> ORGANISM: Artificial Sequence
<220> FEATURE:
<223> OTHER INFORMATION: Nucleotide primer sequence

<400> SEQUENCE: 9
taccttgcag gttgacgccc cggggcacta                                     30
```